United States Patent [19]

Duinker

[11] 4,266,136
[45] May 5, 1981

[54] TOMOGRAPHY WHEREIN SIGNAL PROFILES DERIVED FROM AN OUT-FANNING BEAM OF PENETRATING RADIATION CAN BE RECONSTRUCTED CORRESPONDING WITH PARALLEL INCIDENT RAYS

[75] Inventor: Simon Duinker, Bloemendaal, Netherlands

[73] Assignee: N. V. Optische Industrie "De Oude Delft", Delft, Netherlands

[21] Appl. No.: 28,608

[22] Filed: Apr. 9, 1979

Related U.S. Application Data

[60] Division of Ser. No. 814,989, Jul. 12, 1977, Pat. No. 4,168,435, and a continuation-in-part of Ser. No. 798,672, May 19, 1977, abandoned.

[30] Foreign Application Priority Data

Jul. 19, 1976 [NL] Netherlands .......................... 7607976

[51] Int. Cl.³ ................................................ A61B 6/00
[52] U.S. Cl. .................................. 250/445 T; 364/414
[58] Field of Search ..................... 250/445 T; 364/414

[56] References Cited

U.S. PATENT DOCUMENTS

| 3,983,398 | 9/1976 | Boyd .................................. 250/445 T |
| 4,168,435 | 9/1979 | Duinker ............................. 250/445 T |

Primary Examiner—Alfred E. Smith
Assistant Examiner—T. N. Grigsby
Attorney, Agent, or Firm—O'Brien & Marks

[57] ABSTRACT

Flat out fanning beams of penetrating radiation in the plane of a slice of an object are bounded on one side by an axis of rotation through the object and extend on the other side past the object exterior. These beams are produced at corresponding angles of the rotation and impinge upon a continuous detector surface which is scanned at each angle to generate half profile signals which may then be processed to produce parallized profile signals.

6 Claims, 6 Drawing Figures

TOMOGRAPHY WHEREIN SIGNAL PROFILES DERIVED FROM AN OUT-FANNING BEAM OF PENETRATING RADIATION CAN BE RECONSTRUCTED CORRESPONDING WITH PARALLEL INCIDENT RAYS

CROSS-REFERENCE TO RELATED APPLICATIONS

This application is a divisional application of my copending U.S. application Ser. No. 814,989 filed on July 12, 1977 now Pat. No. 4,168,435 for Method and Apparatus for Tomography Wherein Signal Profiles Derived From an Out-Fanning Beam of Penetrating Radiation can be Reconstructed into Signal Profiles Each Corresponding with a Beam of Parallel Incident Rays. This application is also a continuation-in-part application of my copending U.S. application Ser. No. 798,672 filed May 19, 1977 and now abandoned for Apparatus for Making a Tomogram.

The invention relates to a method and apparatus for forming an image of a lamina of a subject under examination by means of penetrating radiation, such as X-rays, employing a source for producing a substantially flat, out-fanning beam of the penetrating radiation, a support for supporting the subject under examination so that this subject is irradiated by this beam, and a detector device for producing and processing signal profiles which are indicative of the radiation absorption in the lamina of the subject as determined by the beam and are the result of a relative movement between the subject and an assembly including the source of radiation and the detector device.

In the technique known as tomography it is possible to form a density image (tomogram) of a subject under examination that is representative of a "plan view" of a slice-like cross-section (lamina) of this subject. To this end, a relative movement is established between the subject and the assembly including the source of radiation and the detector device, and the subject under examination is irradiated from a series of positions, each position corresponding with a signal profile derived by the detector device. For example, the assembly is rotated about a vertical axis extending through the subject; alternatively, the assembly is stationary and the subject is rotated about this axis.

A tomogram can be reconstructed from a series of signal profiles thus derived by the detector device. It appears that in such a reconstruction the so-called point spread function degrades the definition or resolution of the tomogram. To eliminate this drawback, it has been proposed to preceed the superpositioning of signal profile information, as carried out during the processing of signal profiles provided by the detector device, by a pre-processing of these signal profiles such that the interfering point spread function is eliminated. In this procedure, each original signal profile is opto-electronically pre-processed to provide a new signal profile which, during the reproducing projection, provides a tomogram that is free from the interfering point spread function. It appears that, when use is made of a source of radiation irradiating the subject with a beam of parallel rays, one and the same point spread function applies to all points of the image field. However, the point spread function appears to be position-dependent when the irradiation is performed by means of an out-fanning beam. In other words, when a beam of parallel rays is used an exact correction with respect to the point spread function can be achieved as each original signal profile can be multiplied, fragment by fragment, by a given convolution integral. Such an exact correction and hence optimalization of the resolution cannot be achieved, however, when such a correcting operation is simply applied to a situation in which an out-fanning beam is employed.

For techno-economical reasons, it is unacceptable in the art of tomography to use a beam of parallel rays in a configuration in which the source of radiation is mounted at a relatively great distance from the subject under examination. One should rather contemplate a configuration in which a source for producing a substantially flat, out-fanning beam of radiation is mounted optimally close to the subject.

In the prior art each of the out-fanning beams of radiation had a width so as to irradiate edgewise the full lamina section of the subject and impinge on the detector which included a linear array of discrete detector elements or a continuous strip of detector surface. The array of discrete detector elements is used in computerized tomography where the output signals of these detector elements are subject to an analogue-to-digital conversion and stored. The stored signals are subjected to re-ordering and/or other computer processing to generate signals which can be displayed to produce the tomogram. Analog profile signals derived from scanning the continuous screen type detector can be sampled and digitalized and then processed by the conventional computer techniques, or these analog signals can be subjected to a back projection technique wherein each profile signal is used to deposit parallel lines on a display screen, each line having a uniform intensity corresponding to one respective element of the profile signal, at an angle corresponding to the irradiation angle of the subject. By superimposing sets of these lines on the display screen at the corresponding angles, the tomogram is generated on the display screen. The detector screens of the prior art had to detect a full edgewise image of the object slice under consideration in order to generate the full tomogram image of the slice.

An object of the invention is to provide an apparatus and method which offers advantages of relatively inexpensive construction, fast and reliable operation, improved resolution, etc.

To achieve this object, an apparatus in accordance with the invention bounds a fan-shaped beam of penetrating radiation on one edge at the axis of relative rotation between the object and the radiation source-detector combination so that only one-half of an object slice is irradiated at a corresponding angle. Processing means subsequently convert the analog half profile signals detected by a continuous screen type detector into parallelized profile signals suitable for further processing.

Due to its simple organization, an apparatus according to the invention can be manufactured at a relatively low cost price. Further advantages are, moreover, that relatively little space is required to accommodate the apparatus, and that, as parallel beams are reconstructed from out-fanning beams, the source of radiation can be mounted close to the subject, which permits efficient use of such a source of radiation and a low radiation dose while optimal resolution of the ultimate tomogram is achieved.

The invention will be described in greater detail hereinafter with reference to the accompanying drawings, in which.

Figure 1:
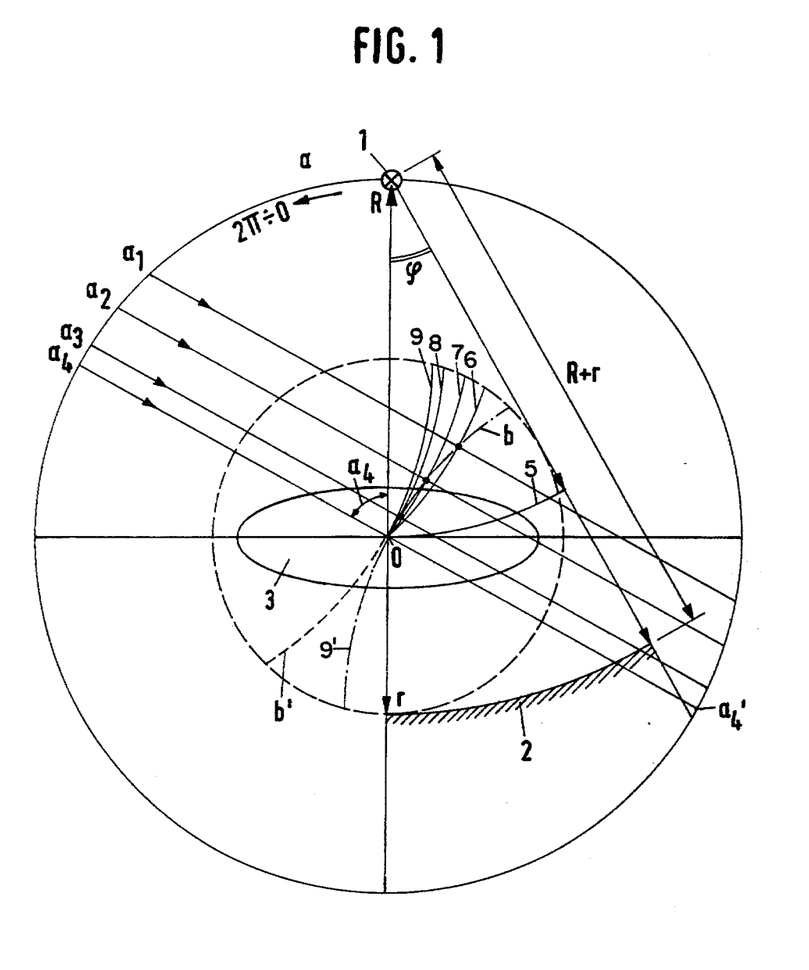
FIG. 1 shows a diagram with reference to which the principle of the present invention will be elucidated.

In the configuration shown in FIG. 1, a source for producing a substantially flat, out-fanning beam of penetrating radiation, such as X-rays, is designated by 1. A capture screen of a detector device is designated by 2. A subject 3 is placed between this capture screen and the source of radiation on a support (not shown). Without the invention being limited thereto, in the configuration shown in FIG. 1 it is assumed for simplicity that an assembly including the source of radiation and the detector device can perform a rotational movement about an axis 0 (normal to the plane of the drawing) extending through the subject, the source of radiation moving along a circular path having radius R. Self-evidently, it is also possible to fixedly mount the assembly and rotate the subject about the axis 0. In both instances it is achieved that the subject can be irradiated from a series of positions on the circular path having radius R. The circular path having radius r is determined by the minimum distance required for an unobstructed rotation of the assembly, including collimators that may be necessary, about the subject under examination, or vice versa.

As will be explained later on, it is an advantage to bound the beam of radiation on one side by a flat plane defined by the axis of rotation extending through the center of rotation 0 and the source of radiation itself. Such a boundary, which has been proposed in Dutch patent application No. 76,05687 too, has the advantages that the angular field of the capture screen as required for the detector device is considerably smaller than the angular field required in the event of an unbounded beam of radiation, and that the spreading of the radiation intensity is less due to the smaller beam width. To avoid image distortion at the edges of the capture screen, it is an advantage to give this screen an arcuate shape, the center of curvature coinciding with the position of the source of radiation and the radius of curvature being R+r. It will be clear that when the capture screen is to concurrently receive a plurality of laminal images of the subject, this capture screen must have a spherical surface. When, in the configuration described above, the subject is irradiated by the out-fanning beam from the source of radiation, at a given position angle of the source-detector assembly relative to the subject a "transmission image" will be projected on the capture screen, while image corresponds with a disc-shaped slice of the subject, the thickness of this slice being determined by the height of the flat beam of radiation and the "length" of the strip-like image being defined by the angular width (angle $\phi$) of the beam.

The detector device, which may be of a known per se type, preferably e.g. a detector device in the form of an X-ray image intensifier, is operative to convert a continuous radiation image in analogue form, e.g. an X-ray image, formed on the capture screen, which image is indicative of the radiation absorption in the respective lamina of the subject from the direction in question (position angle $\alpha$), to a corresponding, intensified electric image signal. After passing a thus-obtained electric image signal through a logarithmic intensifier, a signal is obtained that is representative of the density pattern associated with the lamina of the subject applying to the respective position angle $\alpha$. It will be clear that for a series of position angles $\alpha$, such as $\alpha_1, \alpha_2, \alpha_3, \alpha_4$ etc., a corresponding series of such electric signals can be achieved. After passing through the entire circle having radius R, a group of electric signals is obtained from which an image can be reconstructed that represents the complete density variation within the respective lamina of the subject, provided the angular width (angle $\phi$) of the beam is selected so that each element of the lamina of the subject under examination is irradiated from each position angle $\alpha$. It is observed in this connection that the electric signals (signal profiles) produced by the detector device are the result of using an out-fanning beam of radiation. This means that when during the further processing of such signal profiles it is tried to eliminate the point spread function, no exact correction is possible for the full image field, which means a degradation of the ultimately achieved tomogram.

This drawback can be eliminated by recording the signal profiles provided by the detector device, prior to their further processing, in a separate memory device in a specific manner. Particularly, a signal profile corresponding with each position angle of the source of radiation relative to the subject under examination is recorded as a continuous analogue signal located in accordance with a predetermined path. In order to be able to clearly indicate the direct relationship between the manner of recording and the instantaneous position of the device, an example of such a path is shown in FIG. 1 by the path sections 5, 6, 7, 8 and 9, such a recorded signal profile n corresponding with each position angle $\alpha_n$ of the source of radiation. In the configuration shown in FIG. 1, these signal profiles are recorded in analogue form in accordance with arc-shaped paths having their centre of curvature on the circle having radius R, each of these recorded signal profiles beginning in centre 0 of this circle. Consequently, signal profile 6 corresponding with position angle $\alpha_1$ is achieved by describing a circular arc from centre of curvature $\alpha_1$ at radius R, which arc begins in centre 0. Each of the other signal profiles are recorded in an identical manner, resulting in a bundle of recorded signal profiles beginning in centre 0, so that a collection of vane-like primary signal profiles is obtained.

It appears possible to scan such a collection of recorded primary signal profiles in analogue form in accordance with another collection of paths, in such a manner that by such a scanning a collection of secondary signal profiles can be constructed, in which each of these secondary signal profiles can be taken as being obtained from an imaginary beam of parallel incident rays. This may be appreciated for the primary signal profiles 5–9 shown in FIG. 1 by a closer consideration of this FIG. 1. To this end, this Figure shows a beam of parallel incident rays corresponding with the position angle $\alpha_4$, the primary signal profile fragments corresponding with these parallel incident rays being drawn as the points of intersection of the respective ray and the associated primary signal profile. In other words, the points of intersection between the ray originating from $\alpha_1$ and signal profile 6, the ray originating from $\alpha_2$ and signal profile 7, the ray originating from $\alpha_3$ and signal profile 8 and the ray originating from $\alpha_4$ and signal profile 9. It appears that the thus-obtained points of intersection lie on an arc-shaped path by going through the centre 0 and having a radius of curvature R and a centre of curvature $\alpha'_4$ that it diametrically opposite point $\alpha_4$ that is determinative of the direction of incidence of the respective beam of parallel rays, in other words the centre of curvature $\alpha'_4$ is defined by $\alpha_4 + \pi$. Consequently, the secondary signal profile corresponding with such an arcuate scanning may be regarded as a signal profile derived from a beam of parallel rays. Therefore, each position angle $\alpha_i$ corresponds with a position angle $\alpha'_i$ related thereto and determinative of the arcuate scanning from which a secondary signal profile corresponding with an imaginary beam of parallel rays incident at the angle $\alpha_i$ can be reconstructed. In other words, by such a scanning it is possible to reconstruct from the collection of primary signal profiles the collection of secondary signal profiles, which secondary signal profiles can readily be subjected to a standardized exact correction with respect to the point spread function.

Such scannings should lag the recording of the primary signal profiles by a given angle, e.g. 30°; as all the primary signal profiles to be scanned must have been actually recorded. After scanning the respective group of primary signal profiles, this group may be erased and different information may be recorded in the erased portion of the record medium.

In principle, it is also possible to use a beam of radiation having an angular width twice that shown in FIG. 1. In such a situation, the second half of each primary signal profile should be recorded as schematically indicated by the chain-dotted arc 9', which is possible as the subject under examination is radiation-isotropic, which means that the absorption of the subject along a line depends only on the direction of this line and not on its sense. Self-evidently, in this situation the assembly including the source of radiation and the detector device need only rotate through an angle of $\pi$ radians relative to the subject in order to develop a complete tomogram. The reconstruction of the primary signal profiles thus-recorded by means of a beam of double angular width can be obtained either by scanning through $2\pi$ radians in accordance with "half" arcs b, or by scanning through $\pi$ radians along S-shaped paths, in other words in accordance with mirror-symmetrical arcuate paths b, b'.

The recording of the "half" primary signal profiles in the form of circular arcs going through the origin 0, as discussed with reference to FIG. 1, has the drawback that around this origin the lines of the pattern are difficult to separate, as a result whereof and depending on the manner of scanning to obtain the secondary signal profiles, inaccuracies may occur around this origin. In fact, in the reconstruction of secondary signal profiles corresponding with beams of parallel rays, as discussed above, the scanning is performed practically tangentially to the respective primary signal profiles especially in the vicinity of this origin O, which may lead to an unacceptably high inaccuracy.

Figure 2:
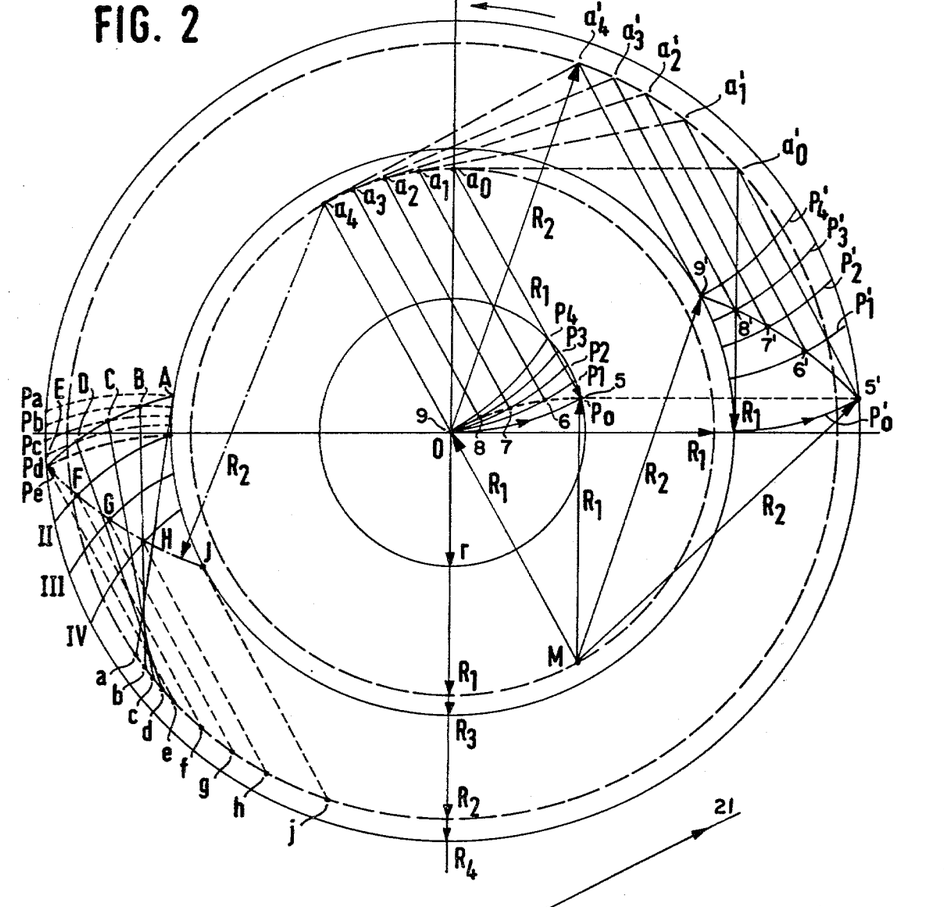
FIG. 2 shows a diagram illustrating a configuration lacking a drawback inherent in the configuration shown in FIG. 1.

To eliminate these drawbacks, consequently it is preferred to draw the primary signal profiles, instead of as vanes originating from the origin O as shown in FIG. 1, as arcuate spokes originating from a rim as schematically shown in FIG. 2. In this FIG. 2, the circle having radius $R_1$ is the path corresponding with a relative movement of the source of radiation with respect to the centre of rotation O. Just as in FIG. 1, the circle having radius r in FIG. 2 is determined by the minimum distance required for an unobstructed rotation about the subject. The distance $R_3$ is the distance through which each time a position angle point $\alpha_1$ is shifted along the tangent to the circle $R_1$ in that point to come to the position angle point $\alpha'_i$ on the circle $R_2$ determinative of the respective primary "half" signal profile $p'_i$, which is recorded as an arc-shaped spoke from a rim having radius $R_3$.

Thus in a manner similar to that employed in the configuration shown in FIG. 1, by means of a series of position angle points, such as $\alpha'_0 \alpha'_4$, a collection of associated primary "half" signal profiles, such as $p'_0$-$p'_4$, is recorded. Without limiting the scope of the invention, the distance $R_3$ is selected so that the locus of the extremities of the primary "half" signal profiles, which originally were on the circle having radius r, are now on a circle having radius $R_4$. In other words, point o of the original primary signal profile $p_o$ becomes the point 5', of the primary signal profile $P'_o$ etc. In FIG. 2, the circle having radius $R_2$ indicates the path of the source points shifted along the tangents through the distances $R_3$. This radius $R_2$ is defined by $R_2 = \sqrt{R_1^2 + R_3^2}$. In the case of a recording as achieved by means of a configuration as shown in FIG. 2, it appears that the reconstruction of the secondary "half" signal profile corresponding with beams of parallel incident rays can be obtained by means of arc-shaped scanning paths having radius of curvature $R_2$ and each time described from the same centre of curvature M corresponding with the point of intersection of the circle about the point of rotation O and having the radius $R_1$ on the one hand and the ray of the parallel beam going through this point O on the other hand. In such a configuration, the points of intersection between the primary signal profiles and the scanning paths for achieving the secondary signal profiles are defined in a better manner. This is schematically shown in FIG. 2 for the position angle point $\alpha_4 + \pi$ and the circular arc determined thereby, which has a radius of curvature $R_2$. The respective points of intersection are indicated by 5', 6', 7', 8' and 9'. These points correspond with a beam of parallel rays incident at an angle $\alpha_4$. It will be clear from the above that as $R_3$ approaches O, the configuration discussed with reference to FIG. 2 changes to the one discussed with reference to FIG. 1. Consequently, self-evidently the arrangement can be made so that each time two "half" profiles are concurrently recorded, as a result whereof a rotation of only $\pi$ radians is required.

Also in the configuration shown in FIG. 2 the scanning operation is delayed with respect to the recording of the primary signal profiles. The surface area within circle $R_3$ is not initially used for recording in the configuration shown in FIG. 2. If the thickness of the annular surface area situated between the circles having radii $R_1$ and $R_3$ can be selected sufficiently small, in which connection the resolution of the selected record medium forms the limit, the collections of primary signal profiles can be recorded in concentric annular areas within one another for a plurality of simultaneous tomograms. It can readily be seen (see in this respect the left-hand part of FIG. 2) that if, instead of drawing the collection of primary signal profiles for a series of discrete position angle values $\alpha_i$, these primary profiles are continuously drawn upon a continuous, preferably uniform, relative rotation of the source about the subject, as will be preferred in practice, the path of the primary profiles drawn will not be determined by circular arcs (Pa, Pb, . . ., Pe) but by involutes (A, B, . . ., E). It can further readily be seen that, nevertheless, by the described scanning in accordance with arc-shaped paths (J, H, . . ., E), again the secondary profile associated with a parallel beam is obtained.

Figure 6:
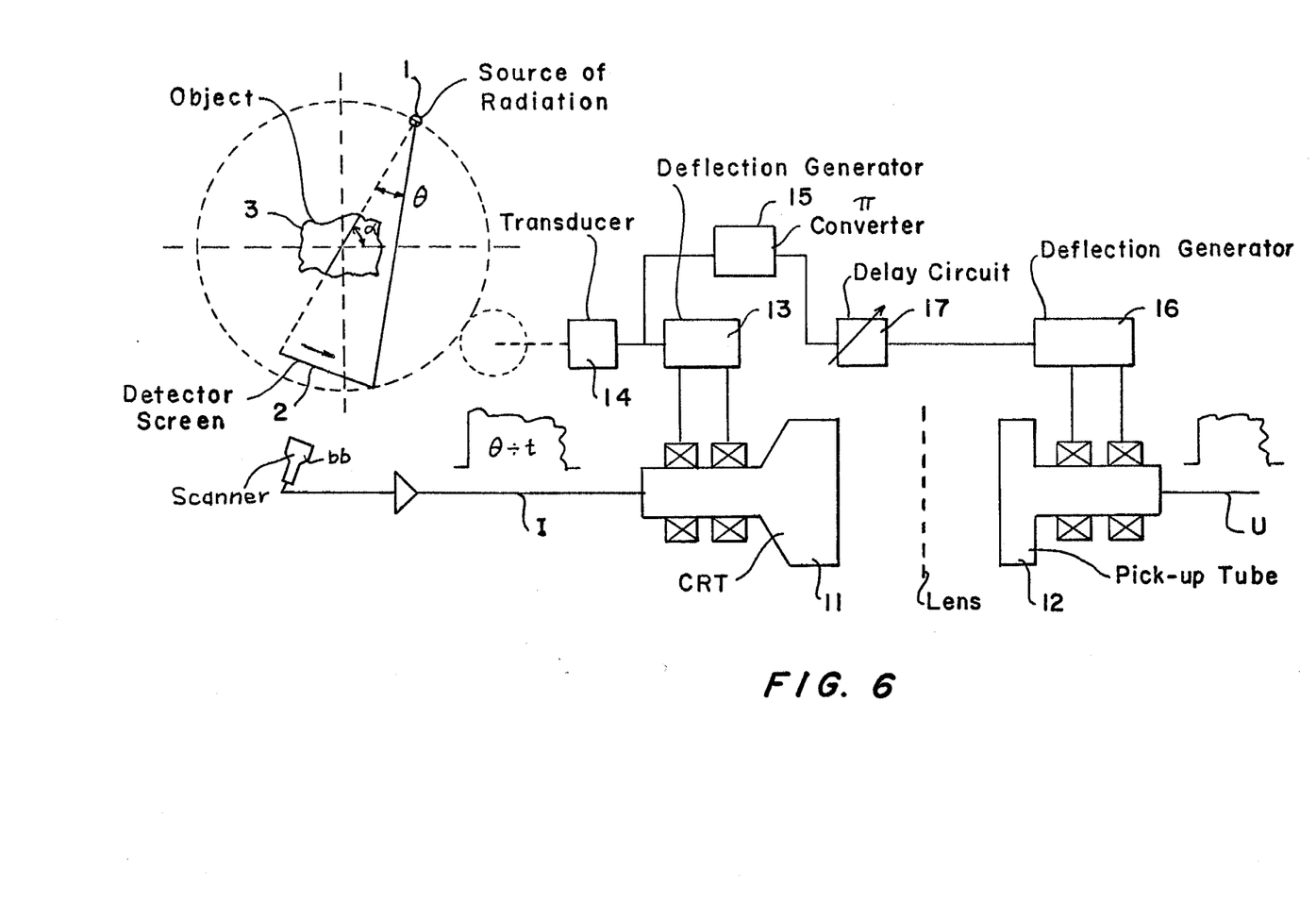
FIG. 6 shows a block diagram of an embodiment of the present invention.

In principle, the invention is not limited to the embodiments adapted to the configuration shown in FIGS. 1 and 2; the general principle of the invention, in which a collection of continuous primary signal profiles as derived by means of a substantially flat, out-flanning beam of radiation is recorded in analogue form in accordance with a given path pattern and a thus-recorded collection is substantially scanned in accordance with another collection of scanning paths having a patttern so that the secondary signal profiles developed from this scanning may be regarded as to be derived by means of a beam of parallel rays, may be illustrated by the basic configuration shown in FIG. 6, in which various variants of the invention may be realized by an appropriate choice of the control functions determining the recording and scanning. In the configuration shown in FIGS. 1 and 2, these control functions are such that the recording of the primary signal profiles is performed in accordance with arc-shaped paths (discontinuous rotation) or in accordance with convolutes such as e.g. hypercycloids (continuous rotation), while the scanning thereof to form the secondary signal profiles is performed in accordance with arc-shaped paths. In general, these control functions may be selected so that both the primary signal profiles and the paths along which these profiles are scanned to produce the secondary signal profiles, form a simple line pattern. For example, there are the following possibilities: the primary signal profiles are recorded in analogue form in accordance with essentially linear paths either in juxtaposed or in superposed relationship, while the scanning is performed in accordance with arcuate paths intersecting the pattern of primary signal profiles; the primary signal profiles are recorded in analogue form in accordance with similar, juxtaposed or superimposed arcuate paths, while the scanning for the reconstruction of the secondary signal profiles is performed along linear paths intersecting the pattern of primary signal profiles; and the primary signal profiles are recorded in analogue form in accordance with essentially linear paths either in juxtaposed or in superimposed relationship, while the scanning is performed in accordance with essentially linear paths intersecting the pattern of primary signal profiles.

Figure 3:
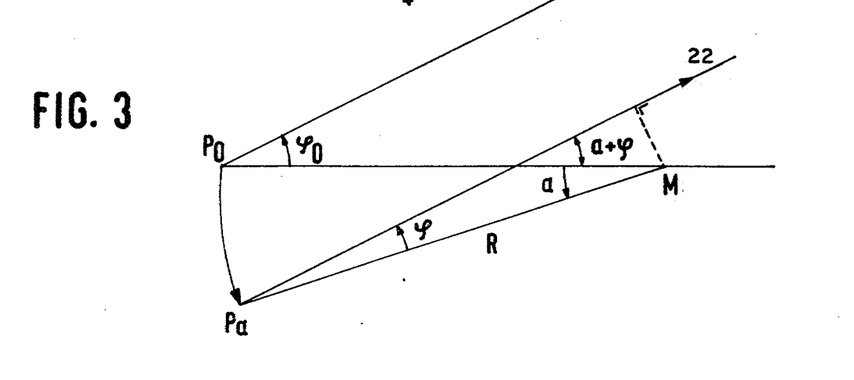
FIGS. 3, 4 and 5 show diagrams with reference to which the principle of the present invention will be discussed for a general instance.

In the situation in which the subject under examination and the assembly including the source of radiation and the detector device are rotated relative to each other, a series of primary signal profiles is obtained which each are a function of the position angle of the source of radiation. The relationship between the primary and secondary signal profiles for this situation will be derived with reference to FIG. 3. In the configuration shown in FIG. 3 it is assumed that the source of radiation moves along an arc-shaped path having radius R about the centre of rotation M from the position $P_o$ to the position $P_\alpha$ etc. By 21 is indicated a ray from the source of radiation when the latter is in position $P_o$, this ray 21 enclosing an angle $\phi_o$ with the line $P_oM$. By 22 is indicated a ray parallel to ray 21 and emanating from the source of radiation when the latter is in the position $P_\alpha$, i.e. after a rotation about centre of rotation M through an angle $\alpha$. The condition that this ray 22 is parallel with the ray 21 is that the sum of the angle $\phi$ enclosed between ray 22 and line $P_\alpha M$ and the angle $\alpha$ is equal to $\phi_o$. In other words, the secondary signal profile associated with direction $\phi_o$ is obtained by measuring the transmission of the ray enclosing an angle $\phi = \phi_o - \alpha$ with the connecting line $P_\alpha M$ upon each angular rotation $\alpha$ of the source of radiation. The distance from this ray to the centre of rotation M is $R.\sin\phi = R.\sin(\phi_o - \alpha)$. The radiation transmission values as measured when an out-fanning beam of radiation is used, e.g. a beam of X-rays, may or may not be logarithmatized, and recorded, for example so that the primary signal profiles derived from this out-fanning beam as a function of the above angle $\phi$, since $\phi$, tangent $\phi$, or in general f ($\phi$), are parallel, straight lines, the spacing of which is proportional to the position angle $\alpha$ of the X-ray source. The secondary profile corresponding with direction $\phi_o$ can then be found as a line through point $\phi = 0$, $\alpha = \phi_o$, and is further characterized by $\alpha + \phi = \phi_o$.

Figure 4:
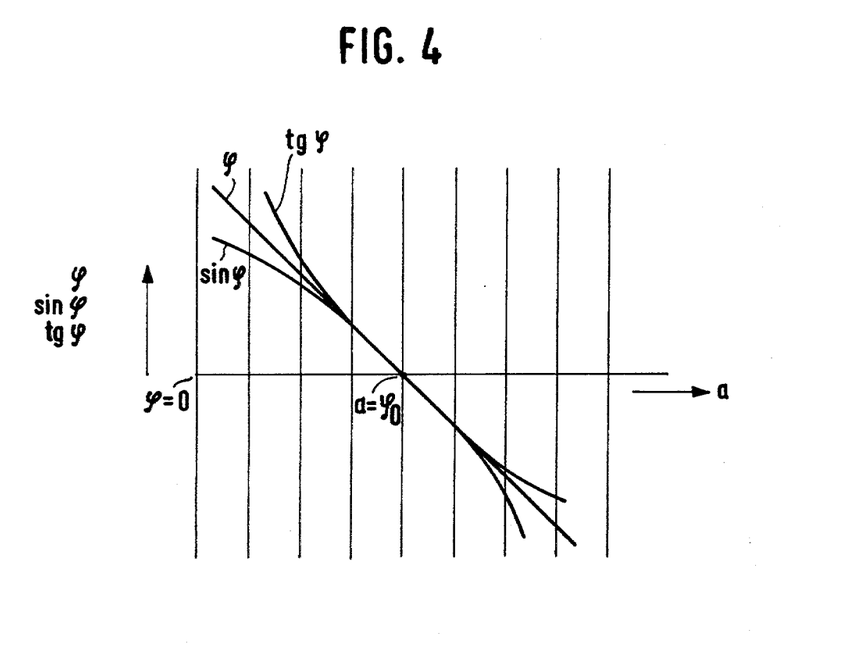

It will be clear that the path along which the scanning is performed for obtaining the secondary signal profile, is a straight line if the primary signal profile derived by measuring by means of an out-fanning beam is recorded as a function of the angle $\phi$, whereas this scanning path followes f($\phi$), if the primary signal profile is recorded as f($\phi$). This is illustrated in FIG. 4.

The secondary signal profiles should be available as a function of the irradiation $\phi$, particularly as a function of the distance $R.\sin \phi$ to the centre of rotation M, which implies that, if the scanning is performed in accordance with the right $\phi$ and, for example, the time is selected to be proportional to this distance, starting from $\phi = 0$, the scanning will have to be performed at increasing rate so as to maintain the first derivative with respect to time of the function sin $\phi$ at a constant value.

The shape of the primary profile as obtained as a function of $\phi$ depends on the geometry of the source of radiation and the detector device, while this shape can be affected further by the optic and optoelectronic distortions.

Figure 5:
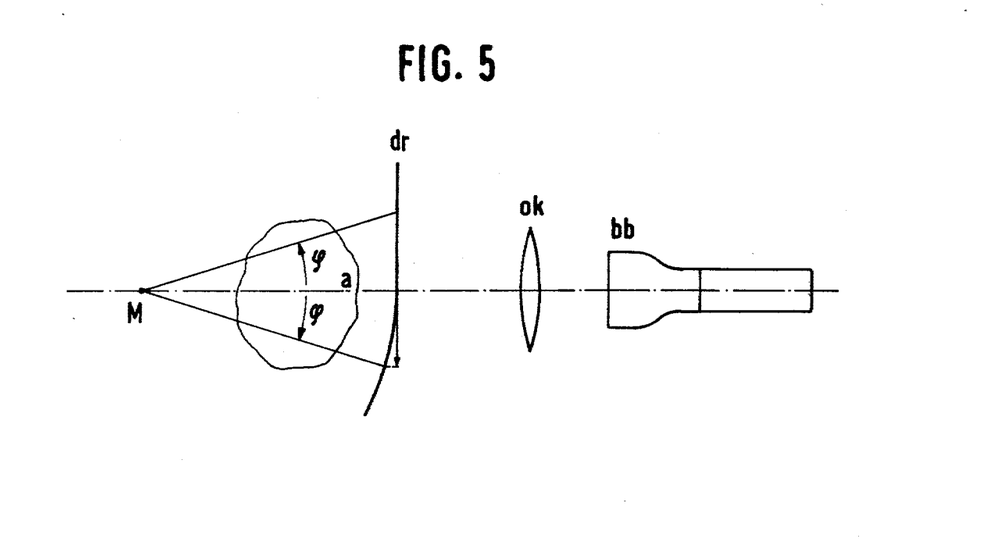

In fact, as appears from FIG. 5, in the event of a flat detector dr the primary profile follows tangent $\phi$, wherein in the event of a curved detector and the source of radiation disposed in a centra of curvature the primary profile follows sine $\phi$. The secondary profiles may, for example, be derived by an appropriate scanning in the image intensifier tube bb receiving the image developed by the detector device through a lens system ok.

In order to obtain an optimally uniform secondary profile, it may be advantageous to record the primary profiles so that the paths have such a width that they are contiguous. An optimalization with respect to the signal-to-noise ratio or the resolution can be obtained by varying the width of the path followed during the scanning of the primary profiles.

In the block diagram of a general embodiment of the invention, as shown in FIG. 6, 11 is a cathode ray tube having a persistent phosphor screen on which the primary profiles, as presented by the electric signals from the scanning of the detector screen, can be recorded. Other recording devices, for example an electronic image converter tube or a continuous two dimensional magnetic sheet memory, may be used. The electric signals derived from the detector device are supplied to input I. A scanner such as TV pickup tube 12 is adapted to coact with the recording device to scan the information recorded in this device, the electric signals obtained as a result of the scanning being developed at output U. The paths along which the information supplied to input I is recorded are determined by a record control device such as a deflection generator 13. This record control depends on position information PI concerning the position or direction from which the subject under examination is irradiated by the source of radiation. In the configuration shown in FIG. 1, the series of positions from which the irradiation is performed is indicated by a circular path about the axis of rotation extending through the subject underexamination. In this configuration the above position information consists of position angles such as $\alpha_1$, $\alpha_2$ etc. Assuming that the size of radius R is also known, the control information required for writing-in the primary signal profiles, which information is to be processed by the record control device 13, is thus complete. Consequently, in response to the position angle information supplied, which information is converted by translator or transducer 14 to corresponding position signals, the record control device 13 supplies control signals to the recording device 11, by means of which control signals the electric input signals supplied to recording device 11 are recorded, for example in accordance with the arc-shaped paths shown in FIG. 1. As stated earlier, by choosing different position information it can be achieved that, by means of the control signals for the recording device 11 as supplied by the record control device 13 as a result thereof, the patterns of recorded primary signal profiles are selectively modified. The position signals produced by translator 14 are supplied to a function converter 15, as a result whereof it is achieved that the control signals intended for the scan control device 16 are related in accordance with a given function to the signals by means whereof the control of device 13 is determined. In the configuration shown in FIG. 1, this relationship is represented by an angular difference $\pi$, so that each position angle $\alpha$ determinative of the control performed by device 13 is associated with a position angle $\alpha + \pi$ determinative of the control performed by device 16. By means of the control action exerted by this device 16 on the scanning device 12 it is achieved that the recorded primary signal profiles are scanned in accordance with the desired paths. In the configuration shown in FIG. 1, these paths are the arc-shaped paths each having a centre of curvature determined by $\alpha + \pi$ and a radius of curvature R. The control signals required for recording the primary signal profiles, as well as the control signals required for the scanning thereof, may be produced in a simple manner, for example, by means of electro-mechanical means serving for the transmission of angular information, which means are coupled to the drive mechanism producing the relative rotation of the subject relative to the assembly including the souce of radiation and the detector device. The output signals obtained from such a scanning as developed at the output U of the scanning device are representative of the secondary signal profiles, which profiles may be regarded as signal profiles produced by the irradiation by means of an imaginary of parallel rays. As explained in the above, the scanning action performed by the scanning device 12 should lag a given period of time with respect to the recording of the primary signal profiles. To this end, a delay device 17 is connected between the function converter 15 and the scan control device 16. If desired, this delay device may be a variable one in order to permit selective adjustment of the delay and adaptation thereof to the conditions of operation.

Output signal U produced by the scanning device 12 is readily suited for further processing. As an exact correction with respect to the point spread function has been performed previously, a high resolution tomogram can readily be obtained therefrom by superposition, in spite of the fact that a source of radiation producing an out-fanning beam is used. Although, primarily, the practical realization of the present apparatus will involve tomographic image reconstruction in analog manner, of course it is readily possible to digitalize the output signals U and to perform the image reconstruction point-by-point by means of a computer. The latter procedure may prove advantageous if not the entire cross-section but only specific parts thereof are considered of interest.

I claim:

1. An apparatus for generating parallelized profile signals of a slice of an object, comprising;
    an X-ray source on one side of the object for generating a fan-shaped beam of X-ray radiation intercepting only one-half of a slice shaped section of the object,
    detector means on the opposite side of the object and having a detector surface extending so as to intercept the fan-shaped beam to produce analog half profile signals,
    means for effecting relative rotation between the object and the combination of the source and the detector means through a complete revolution about the object perpendicular to the fan-shaped beam,
    said X-ray source and said detector means being arranged so that the fan-shaped beam has one side edge at the axis of rotation and has the other side edge outside of the object, and
    processing means coupled to the detector means for converting the analog half profile signals from the detector means into parallelized profile signals.

2. An apparatus according to claim 1, wherein said detector surface is a continuous X-ray screen.

3. An apparatus according to claim 1, wherein said detector surface is a continuous X-ray screen, and said detector means includes an image intensifier tube and optical means for depicting the detector surface on the photocathode of said image intensifier tube.

4. An apparatus according to claim 1, wherein the combination of the X-ray source and the detector surface is stationary, and the means for effecting relative rotation between said object and said combination are means for rotating the object relatively to said combination.

5. Apparatus according to claim 1, wherein the means for effecting relative rotation between said object and said combination of the X-ray source and said detector surface are means for rotating said combination around said object.

6. A method of producing parallelized profile signals of a slide of an object comprising the steps of:
    placing the object so as to only partially extend between an X-ray source and a detector surface of detecting means,
    producing relative rotation between the object and the combination of the X-ray source and the detector surface through a complete revolution about an axis extending centrally through the object, projecting fan-shaped beams of X-ray radiation from the X-ray source at respective angles during the rotation, each beam irradiating a respective one-half of a sliced shaped section of the object so that each beam is perpendicular to the axis and has one edge contiguous the axis and has the other edge extending outside of the object, and detecting, by means of the detecting means, the beams passing through the respective half slices to generate analog half profile signals, and processing the analog half profile signals to produce parallelized profile signals.

* * * * *